(12) United States Patent
Bakalos

(10) Patent No.: US 10,568,678 B2
(45) Date of Patent: Feb. 25, 2020

(54) NEUTRAL DRIVE FEEDBACK LOOP COMPENSATION FOR DETECTED ELECTROSURGICAL UNIT SIGNAL

(71) Applicant: Draeger Medical Systems, Inc., Andover, MA (US)

(72) Inventor: Pericles Nicholas Bakalos, Maynard, MA (US)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 442 days.

(21) Appl. No.: 15/382,449

(22) Filed: Dec. 16, 2016

(65) Prior Publication Data

US 2018/0168708 A1 Jun. 21, 2018

(51) Int. Cl.
*A61B 18/12* (2006.01)
*A61B 18/00* (2006.01)
(Continued)

(52) U.S. Cl.
CPC ............ *A61B 18/00* (2013.01); *A61B 5/0402* (2013.01); *A61B 5/0408* (2013.01); *A61B 5/6824* (2013.01); *A61B 5/6828* (2013.01); *A61B 5/7217* (2013.01); *A61B 18/16* (2013.01); *A61N 1/3931* (2013.01); *A61B 5/04017* (2013.01);
(Continued)

(58) Field of Classification Search
CPC .............. A61B 5/7217; A61B 5/04012; A61B 5/01017; A61B 5/0402; A61B 5/0428; A61B 5/04288; A61B 18/1233; A61B 18/16; A61B 2018/00839; A61B 2018/00869; A61B 2018/00642; A61B 2018/00892; A61B 2018/1293; A61B 5/04017; A61B 5/0408; A61B 5/6824; A61B 5/6828; A61N 1/08; A61N 1/323; (Continued)

(56) References Cited

U.S. PATENT DOCUMENTS 4,934,377 A * 6/1990 Bova .................. A61B 5/04004
600/509
6,438,406 B2 * 8/2002 Yonce .................. A61B 5/0428
128/901
(Continued)

FOREIGN PATENT DOCUMENTS

WO 2015/153426 A1 10/2015
WO WO-2015153426 A1 * 10/2015 ........... A61B 5/7203

OTHER PUBLICATIONS

Lowe, Doug. Electronics Components: How to Use and Op Amp as a Voltage Comparator. Sep. 4, 2016. http://www.dummies.com:80/programming/electronics/components/electronics-components-how-to-use-an-op-amp-as-a-voltage-comparator/ (Year: 2016).*
(Continued)

*Primary Examiner* — Thomas A Giuliani
(74) *Attorney, Agent, or Firm* — Wenderoth, Lind & Ponack, L.L.P.

(57) ABSTRACT

Methods and apparatuses are provided for neutral drive feedback loop compensation of detected electrosurgical unit signals. An apparatus includes an electrosurgery unit (ESU) signal detection circuit, a compensation switch, and an ESU filter switch. Both switches activate based on an output of the ESU signal detection circuit. A neutral drive feedback loop circuit is configured to compensate for a phase change characteristic of an ESU filter circuit.

22 Claims, 15 Drawing Sheets

(51) Int. Cl.
| | |
|---|---|
| *A61B 5/00* | (2006.01) |
| *A61B 5/0402* | (2006.01) |
| *A61B 5/0408* | (2006.01) |
| *A61B 18/16* | (2006.01) |
| *A61N 1/39* | (2006.01) |
| *A61B 5/04* | (2006.01) |

(52) U.S. Cl.
CPC .............. *A61B 2018/00642* (2013.01); *A61B 2018/00678* (2013.01); *A61B 2018/00839* (2013.01); *A61B 2018/00869* (2013.01); *A61B 2018/00892* (2013.01); *A61B 2018/1293* (2013.01)

(58) Field of Classification Search
CPC . A61N 1/36125; A61N 1/3704; A61N 1/3931
USPC .................................. 606/32, 34, 35, 38, 42
See application file for complete search history.

(56) References Cited

U.S. PATENT DOCUMENTS

| | | |
|---|---|---|
| 6,985,883 B1 | 1/2006 | Togher et al. |
| 8,108,039 B2 | 1/2012 | Saliga et al. |
| 8,641,708 B2 * | 2/2014 | Govari ............... A61B 18/1492 606/41 |
| 2008/0281322 A1 * | 11/2008 | Sherman ............ A61B 18/1492 606/42 |
| 2009/0018429 A1 * | 1/2009 | Saliga ................ A61B 5/04004 600/407 |
| 2010/0324618 A1 * | 12/2010 | Wanasek ............. A61N 1/3625 607/9 |
| 2011/0213227 A1 * | 9/2011 | Ziv ...................... A61B 5/0002 600/323 |
| 2013/0237874 A1 | 9/2013 | Zoicas |
| 2014/0148802 A1 * | 5/2014 | LeMay .............. A61B 18/1233 606/33 |
| 2016/0228018 A1 | 8/2016 | Mahon et al. |

OTHER PUBLICATIONS

Extended European Search Report for European Application No. 16207509.7 dated Oct. 26, 2017 (3 pages).
"Frequency compsentation," Wikepedia: The Free Encyclodpedia. Retrieved from the internet URL:https://en.wikipedia.org/wiki/Frequency_compensation, retrieved on Sep. 9, 2016, 4 pages.

* cited by examiner

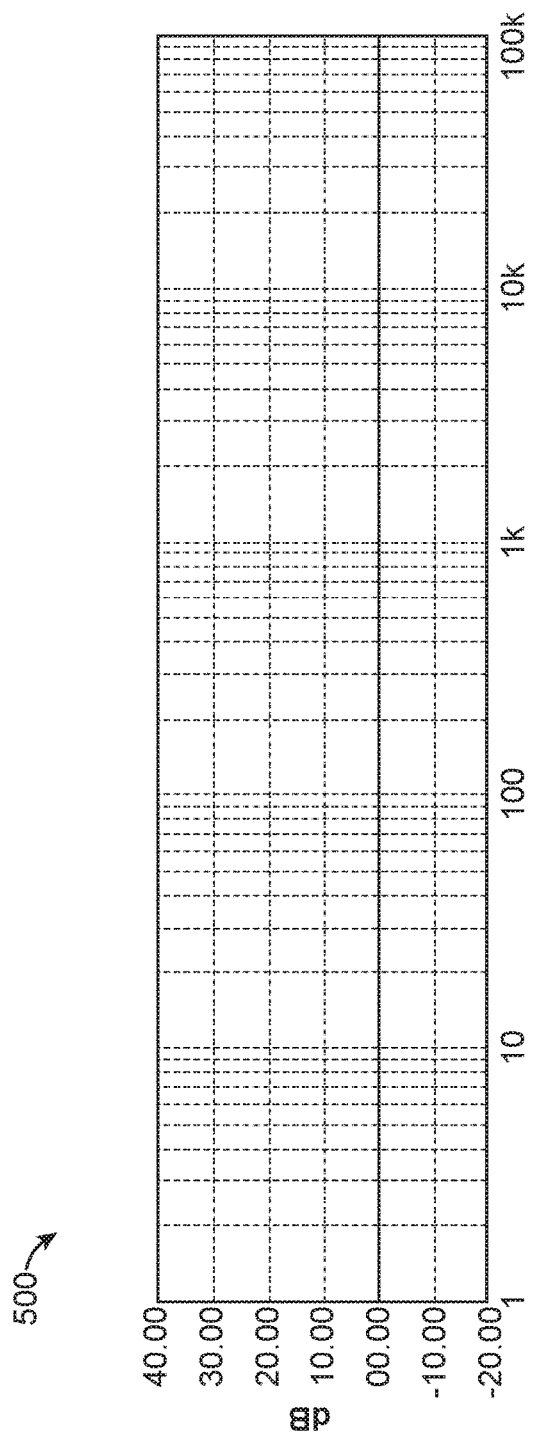
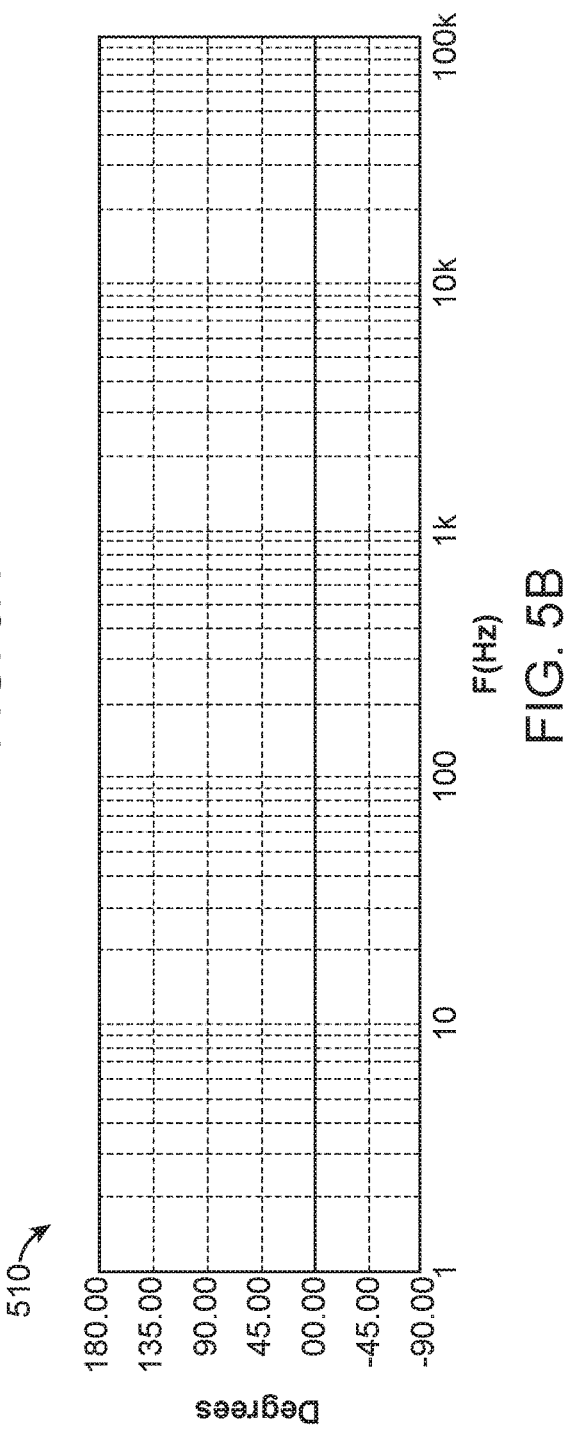
FIG. 5A
FIG. 5B

NEUTRAL DRIVE FEEDBACK LOOP COMPENSATION FOR DETECTED ELECTROSURGICAL UNIT SIGNAL

TECHNICAL FIELD

The subject matter described herein relates to generally to electrical circuits, and, more specifically, to neutral drive feedback loop compensation circuits.

BACKGROUND

Electrosurgical units (ESU) are routinely used in operating rooms and are known to interfere with the monitoring of patients' bio-potential signals (e.g. electrocardiogram signals, electroencephalography signals, blood pressure, etc.). An ESU applies a large amplitude (e.g., 100 V-5 kV) and high frequency (>300 kHz) signal to a patient's body for operations. However, the ESU signal may also have energy at lower frequencies (e.g., from direct current to 100 Hz) because the high-frequency ESU signal amplitude is modulated due to cutting and subsequently rectified when a current passes through ESU electrodes. As a result, the lower frequency components of the ESU signal may generate noises in the pass band of bio-potential signals of interest. Such noise often produces false alarms (e.g., a high heart rate) in software algorithms that monitor the bio-potential signals.

SUMMARY

In one aspect, an apparatus includes an ESU signal detection circuit, a compensation switch, and an ESU filter switch. Input to the ESU signal detection circuit can be a voltage level from an electrocardiogram (ECG) electrode affixed to a patient. The compensation switch and the ESU filter switch are both electrically coupled to an output of the ESU signal detection circuit. The ESU signal detection circuit can include a peak voltage detector, a threshold circuit, and an ESU signal operational amplifier.

Based on an active compensation switch, a neutral drive feedback loop circuit is configured to compensate for a phase change characteristic of an ESU filter circuit activated by the ESU filter switch. A frequency response of the neutral drive feedback loop circuit can compensate for the phase change characteristic. The phase change characteristic can be, for example, a dominant pole.

In some variations, the apparatus can also include a patient monitor. In other variations, the apparatus can include a plurality of ECG electrodes. The plurality of ECG electrodes affixed to the patient can include a right arm electrode, a left arm electrode, and a left leg electrode.

The peak voltage detector can be configured to measure an ESU voltage level. The peak voltage detector can include a series resistor-capacitor (RC) circuit. An electrode input signal can be connected to a resistor of the series RC circuit. The peak voltage detector can include a parallel inductor diode circuit having a first diode and an inductor. The parallel inductor diode circuit can be electrically coupled between a capacitor of the series RC circuit and earth ground. The peak voltage detector can also include a second diode electrically coupled in series with the parallel inductor diode circuit. An anode end of the second diode can be connected to a cathode end of the first diode. The peak voltage detector can include a parallel RC circuit electrically coupled between a cathode end of the second diode and earth ground. The measured ESU voltage level can be measured across the parallel RC circuit.

In some variations, the peak voltage detector circuit can be frequency selective with a maximum sensitivity range of about 100 kHz to 1 MHz.

The threshold circuit can be configured to set a threshold voltage for comparison with the measured ESU voltage level. The ESU signal operational amplifier can be configured to compare the threshold voltage and the measured ESU voltage level. An inverting input of the ESU signal operational amplifier can be connected to the threshold voltage and an non-inverting input of the ESU signal operational amplifier can be connected to the measured ESU voltage level. The activation of the compensation switch and the ESU filter switch can be based on an output of the ESU signal operational amplifier. For example, a high output of the ESU signal operational amplifier can activate the compensation switch and the ESU filter switch.

The neutral drive feedback loop circuit can include a first operational amplifier and a second operational amplifier. Each operational amplifier can have at least one inverting input, at least one a non-inverting input, and at least one output The neutral drive feedback loop circuit can include a compensation circuit, a first and second resistor, a first operational amplifier, and a second operational amplifier, each operational amplifier having an inverting input, a non-inverting input, and an output. A parallel resistor-capacitor (RC) circuit electrically can be coupled between an input of the neutral drive feedback loop circuit and a first resistor. The first resistor can be coupled between the parallel RC circuit and earth ground at a first coupling point. The first coupling point can be connected to the non-inverting input of the first operational amplifier. A series RC circuit can be electrically coupled in parallel to a second resistor. The second resistor coupled in series with the output of the first operational amplifier and the inverting input of the second operational amplifier.

A first circuit can be electrically coupled in parallel between the non-inverting input of the second operational amplifier and the output of the second operational amplifier. The first circuit can include at least five resistors and at least three capacitors. An output resistor having a first output terminal and a second output terminal can be electrically coupled to the second operational amplifier. The first output terminal is electrically coupled to the output of the second operational amplifier. An output of the neutral drive feedback loop circuit can be the second output terminal.

In some variations, input into the neutral drive feedback circuit can be an average voltage level of an ECG electrode set affixed to a patient. The output of the neutral drive feedback circuit can be a current that is provided to an ECG electrode affixed to a patient.

The compensation circuit can include a first resistor having a first terminal and a second terminal. The compensation circuit can also include a second resistor having a first terminal and a second terminal. The second terminal of the first resistor can be electrically coupled to the first terminal of the second resistor at a first coupling point. The compensation circuit can also include a first series RC circuit electrically coupled in parallel on a resistor end to the first coupling point. The compensation circuit can include a second RC circuit electrically coupled to in parallel on a resistor end to the first terminal of the first resistor. Capacitor ends of the first series RC circuit and the second series RC circuit can be electrically coupled to the compensation switch. The compensation switch can be electrically coupled to earth ground. The first end of the first resistor and the second end of the second resistor can be each coupled to the neutral drive feedback loop circuit.

The ESU filter circuit can include at least two resistors, a first and a second diode, a capacitor, and an ESU filter switch. The at least two resistors can be electrically coupled to one another in series. The at least two resistors can be defibrillator protection resistors. The first diode and the second diode can be electrically coupled to one another in series at a coupling point. The coupling point can be at an anode end of the first diode and a cathode end of the second diode. The at least two resistors can be electrically coupled to the first diode and the second diode at the coupling point. The capacitor can have one end electrically coupled to the coupling point and another end electrically coupled to the ESU filter switch. The ESU filter switch can be electrically coupled between another end of the capacitor and a signal ground.

In some variations, input to the ESU filter circuit can be a voltage level from an ECG electrode affixed to a patient. The output of the ESU filter circuit can be a voltage level provided to a patient monitor.

In another aspect, a method for neutral drive feedback loop compensation of a detected electrosurgical unit signal includes monitoring a plurality of ECG electrodes affixed to the patient for an ESU signal. A phase change characteristic of the ESU filter circuit is compensated for by activating a neutral drive feedback loop circuit based on an active compensation switch. A compensated signal from the neutral drive feedback loop circuit is output to the to the right leg electrode.

In some variations, monitoring of the ECG electrodes can include detecting an ESU signal using an ESU detection circuit. An ESU filter switch and a compensation switch can be activated based on an output of the ESU signal detection circuit.

The subject matter described herein provides many technical advantages. One technical advantage includes providing for automatic noise compensation based on ESU signal detection. Additionally, the subject matter described herein provides for the simultaneous usage of a neutral drive feedback loop with an active ESU filter circuit to compensate for a detected ESU signal.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIG. 5A is an example magnitude plot of the frequency response of an inactive compensation circuit;

FIG. 5B is an example phase plot of an inactive compensation circuit;

DETAILED DESCRIPTION

The interference of an ESU with bio-potential signal monitoring can be problematic. For example, false alarms may be produced when an ESU is in use, but alarm mechanisms may not be turned off to prevent such false alarms because the alarm mechanisms are still needed in between the use of the ESU. Software algorithms may be developed to detect an ESU in operation, but such algorithms may be inherently limited by the sampling rate of an analog to digital converter (ADC) used for converting ESU signals to digital signals. Usually the sampling rate of the ADC is too low to detect high-frequency ESU signals which are often in the MHz range.

The systems and methods described herein can be configured to implement various mechanisms for detecting whether an ESU is active. For example, the unique high frequency nature of ESU signals, usually separated from bio-potential signal related frequencies by more than two orders of magnitude, renders the high frequency ESU signals available for detection.

Figure 1:
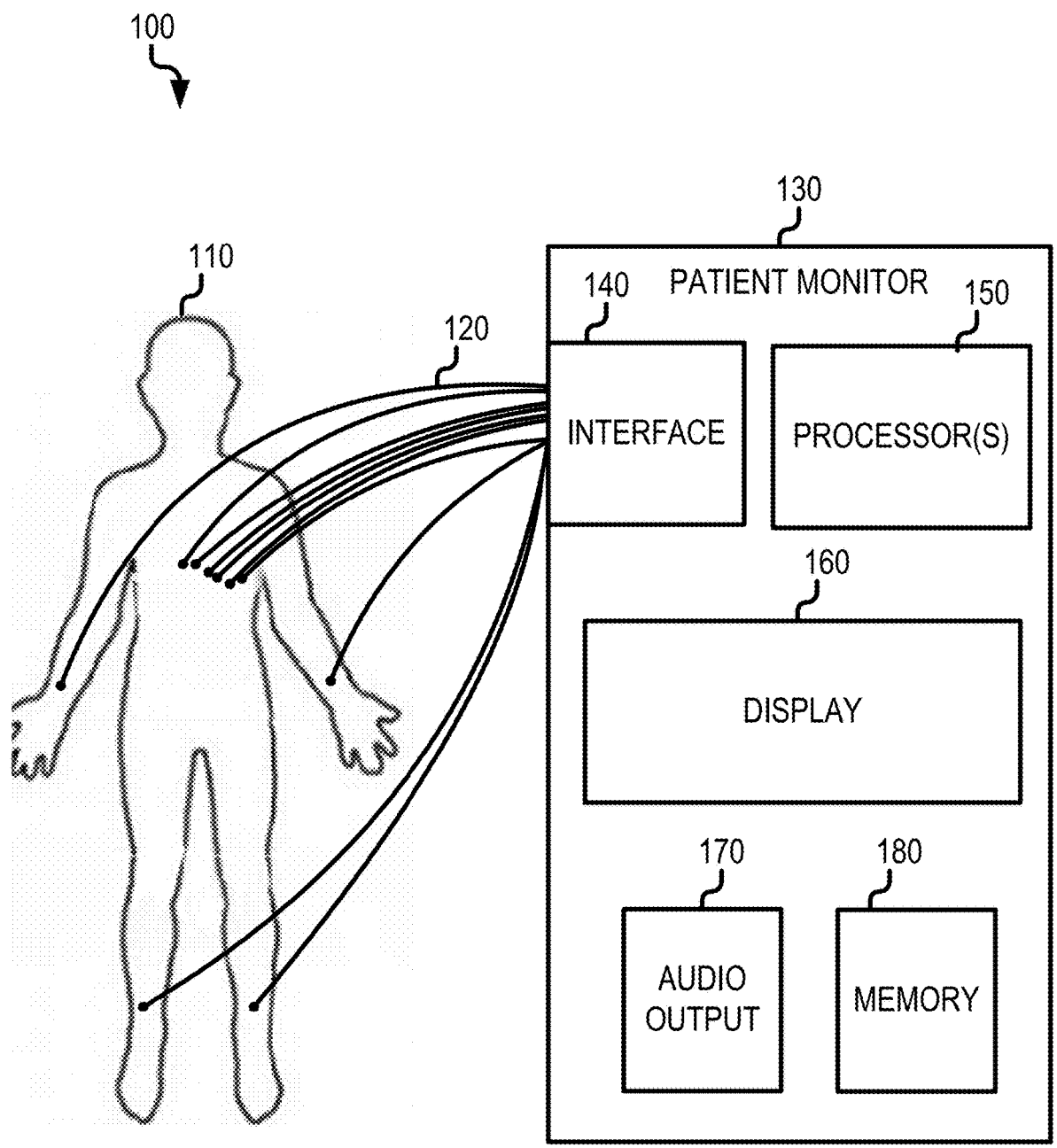
FIG. 1 is a diagram illustrating an example implementation in which ECG data from a patient is measured by a patient monitor.

FIG. 1 is a diagram 100 illustrating an example implementation in which electrocardiogram (ECG) data from a patient 110 is measured by a patient monitor 130. The patient monitor 130 can include memory 180 for storing instructions for execution by one or more processor/processor cores 150. Memory 180 can also be capable of storing data. The patient monitor 130 can include a display 160 for rendering visual information that corresponds to the ECG data and patient vital signs (e.g., values, waveforms, etc.). In addition, the patient monitor 130 can also include an interface 140 that permits for wired or wireless communication with one or more electrodes of an electrode set 120 and/or a remote medical device and/or a remote computing system or network to transmit/receive data pertaining to ECG data and the like. Electrode set 120 can include, for example, a right arm electrode, a left arm electrode, and a left leg electrode. Patient monitor 130 can transmit data characterizing the ECG data of the patient 110 to a remote computing system (e.g., medical device, back-end computing system, etc.) via the interface 140. Patient monitor 130 can also include an audible alarm that can sound from an audio output 170 alerting a patient and/or medical staff.

Figure 2:
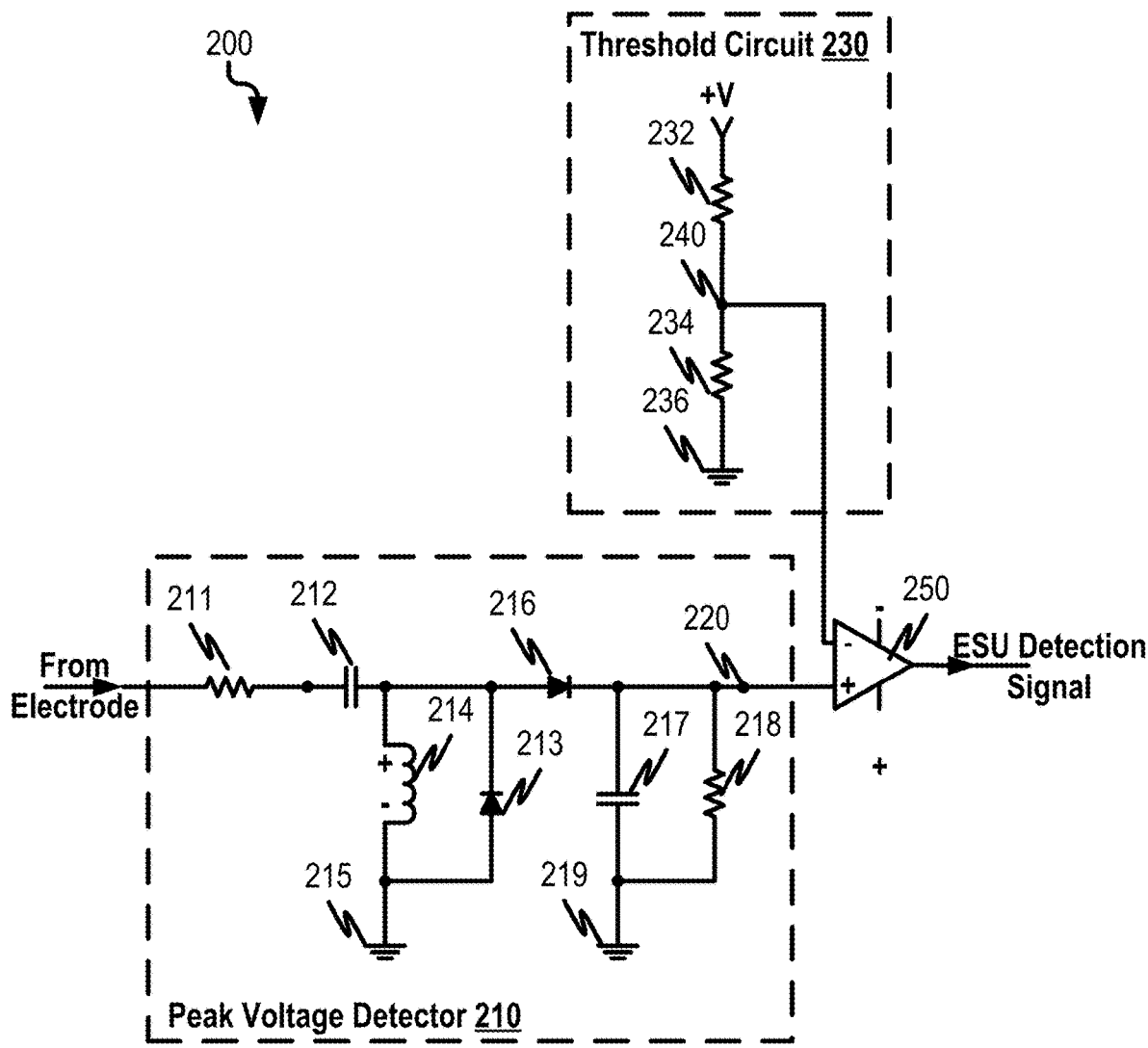
FIG. 2 is an example ESU signal detection circuit.

FIG. 2 depicts an example ESU signal detection circuit 200. ESU signal detection circuit 200 can have an input signal from an electrode of electrode set 120 electrically coupled to patient 110 and an output signal that indicates the detection of an ESU voltage in the input signal. ESU signal detection circuit 200 can include peak voltage detector 210, threshold circuit 230, and ESU signal operational amplifier 250. Peak voltage detector 210 can be configured to measure an ESU voltage level at measuring point 220. The ESU voltage level at measuring point 220 can be a Direct Current (DC) voltage level.

Threshold circuit 230 can be configured to set a threshold voltage measured at a threshold point 240 for comparison with the ESU voltage level at measuring point 220. The voltages at threshold point 240 and measuring point 220 can be compared using ESU signal operational amplifier 250. Threshold point 240 can be electrically coupled with an inverting input of ESU signal operational amplifier 250. Measuring point 220 can be electrically coupled with a non-inverting input of ESU signal operational amplifier 250. Operational amplifier 250 is used as a comparator to compare voltage levels at measuring point 220 and threshold point 240. A high output of ESU signal operational amplifier 250 can indicate that an ESU signal has been detected within the input signal.

Peak voltage detector 210 can be frequency selective with a maximum sensitivity ranging between 100 kHz to 1 MHz. Peak voltage detector 210 can include a series resistor-capacitor (RC) circuit having resistor 211 and capacitor 212 electrically coupled with one another in series. An input signal can be electrically coupled to an end of resistor 211. This input signal can be from one or more electrodes of electrode set 120 electrically coupled to patient 110. An end of capacitor 212 can be electrically coupled to a parallel inductor diode circuit having diode 213 and inductor 214 coupled to one another in parallel. The anode end of diode 213 can be electrically coupled to earth ground 215. The cathode end of diode 213 can be electrically coupled to an end of inductor 214. The other end of inductor 214 can also be electrically coupled to earth ground 215. The cathode end of diode 213 can be electrically coupled to an anode end of another diode 216. The cathode end of diode 216 can be electrically coupled to a parallel RC circuit having capacitor 217 and resistor 218 electrically coupled with one another in parallel. One end of the parallel RC circuit can be electrically coupled to earth ground 219. The other end of the parallel RC circuit provides measuring point 220 where an ESU voltage level can be measured.

Threshold circuit 230 can include resistor 232 and resistor 234 electrically coupled to one another in series at threshold point 240. One end of resistor 232 can be electrically coupled to an input voltage, +V. An end of resistor 234 can be electrically coupled to earth ground 236.

Figure 3:
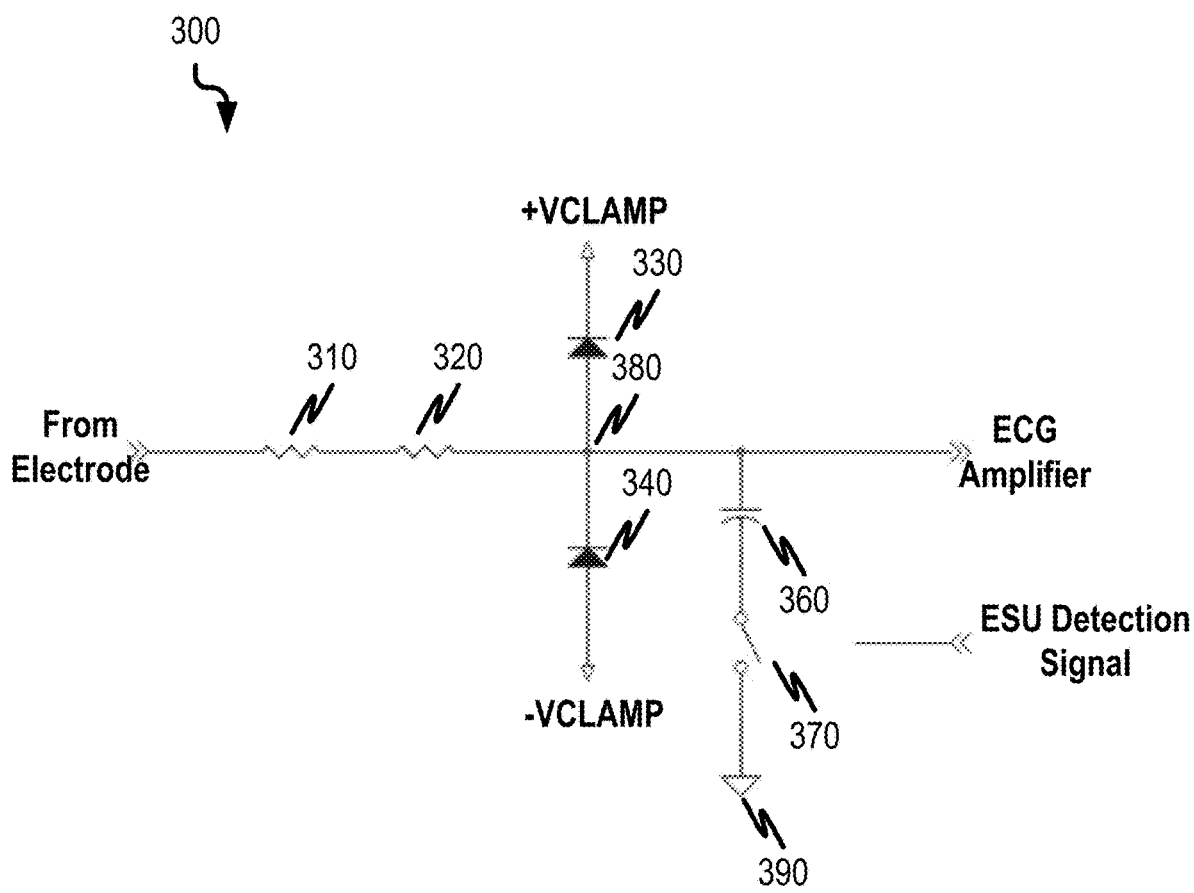
FIG. 3 is an example ESU filter circuit.

FIG. 3 depicts an example ESU filter circuit 300. ESU filter circuit 300 can have an input signal from an electrode of electrode set 120 electrically coupled to patient 110 and an output signal that goes to an ECG amplifier. ESU filter circuit 300 can include resistors 310, 320, diodes 330, 340, capacitor 360, and ESU filter switch 370. When activated, ESU filter circuit 300 is a first order RC low pass filter network. The input signal from an electrode can be electrically coupled to one end of resistor 310. The other end of resistor 310 can be electrically coupled in series with resistor 320. Resistors 310, 320 can be defibrillation protection resistors, for example, each having a resistance value of 10 kΩ.

ESU filter switch 370 can be activated to close upon detection of an ESU signal. Closing of ESU filter switch 370 switches capacitor 360 into ESU filter circuit 300. ESU filter switch 370 remains open when there is no ESU filter signal detection such that capacitor 360 is not connected to signal ground 390 to provide a path for high frequency currents to flow to ground. When ESU filter switch 370 is open, high frequency currents, for instance due to an ESU signal, would flow directly into an ECG amplifier.

An end of resistor 320 can be electrically coupled to diodes 330, 340 via coupling point 380. The anode end of diode 330 can be electrically coupled to coupling point 380, with the cathode end of diode 330 electrically coupled to a positive clamped voltage, +VCLAMP. The cathode end of diode 340 can be electrically coupled to coupling point 380, with the anode end of diode 340 electrically coupled to a negative clamped voltage, −VCLAMP. Capacitor 360 can be electrically coupled in parallel to diode 340. ESU filter switch 370 can be electrically coupled in series between capacitor 360 and signal ground 390. ESU filter switch 370 can be electrically coupled to an output of ESU signal detection circuit 200.

Figure 4:
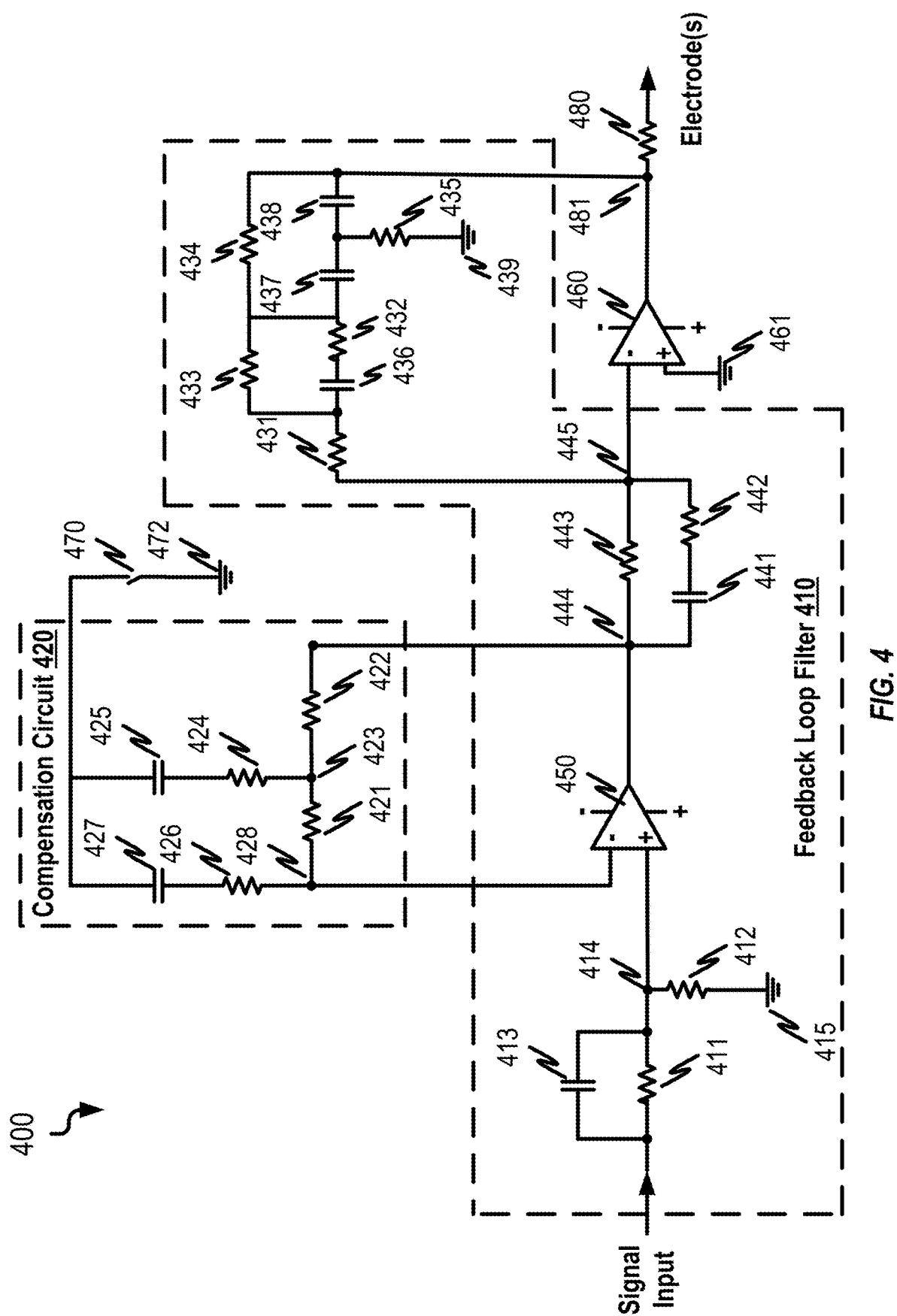
FIG. 4 is an example neutral drive feedback loop circuit.

FIG. 4 depicts an example neutral drive feedback loop circuit 400. Neutral drive feedback loop circuit 400 can have a signal input from one or more electrodes of electrode set 120. In one example, the signal input can be an average voltage level of electrode set 120 affixed to patient 110 such as a Wilson Average input as described in WO 2015/153426, filed Mar. 30, 2015, entitled "Detecting Saturation in an Electrocardiogram Neutral Drive Amplifier," the entire contents of which are incorporated by reference herein. In another example, the signal input can be a voltage level from an electrode of electrode set 120 affixed to a patient 110. Due to a high gain of neutral drive feedback loop circuit 400, error associated with the Wilson Average input is forced to zero.

An output signal of neutral drive feedback loop circuit 400 can be connected to an electrode of electrode set 120. The output signal can be, for example, a current which is provided to an electrode of electrode set 120 affixed to patient 110.

Neutral drive feedback loop circuit 400 can include a compensation circuit 420, a feedback loop filter circuit 410, operational amplifier 460, a compensation switch 470, and a resistor 480. Feedback loop filter circuit 410 provides for feedback from an electrode response of an electrode of electrode set 120 incorporating the ESU filter circuit 300 response. Compensation circuit 420 is a high pass filter having a unity gain at low frequencies and a high gain at frequencies above the ESU filter circuit 300 pole frequency.

The neutral drive feedback loop circuit 400 can be configured, based on compensation switch 470 being in an active state, to compensate for a phase change characteristic of an ESU filter circuit 300. The phase change characteristic, for example, can be a dominant pole of ESU filter circuit 300.

Compensation circuit 420 can include a resistor 421 and a resistor 422 electrically coupled in series at a coupling point 423. A series RC circuit having a resistor 424 and a capacitor 425 can be electrically coupled to resistors 421, 422. One end of resistor 424 can be electrically coupled to resistors 421, 422 at coupling point 423. An end of capacitor 425 can be electrically coupled to compensation switch 470. Another series RC circuit, having a resistor 426 and a capacitor 427 can be electrically coupled to another end of resistor 421 at a coupling point 428. An end of capacitor 427 can also be electrically coupled to compensation switch 470. Compensation switch 470 can be electrically coupled between capacitors 425, 427 and earth ground 472.

Compensation switch 470 can be electrically coupled to an output of ESU signal detection circuit 200. Based on a high output of ESU signal operational amplifier 250, the compensation switch 470 can be activated and connect an end of capacitors 425, 427 to earth ground 472. The connection activates the compensation circuit 420. Compensation circuit 420 can be electrically coupled to an inverting input of operational amplifier 450 via coupling point 428.

Feedback loop filter 410 can include resistors 411, 412, 431, 432, 433, 434, 435, 442, 443, and capacitors 413, 441, 436, 437, 438. Resistor 411 and capacitor 413 can be electrically coupled to one another in a parallel RC circuit. A signal input can be electrically coupled to one end of the parallel RC circuit. Resistor 412 can be electrically coupled between another end of the parallel RC circuit at coupling point 414 and earth ground 415. Coupling point 414 can be electrically coupled to a non-inverting input of operational amplifier 450.

Capacitor 441 and resistor 442 can be electrically coupled in series with one another. One end of capacitor 441 can be electrically coupled to an end of resistor 443 at coupling point 444. An end of resistor 442 can be electrically coupled to an end of resistor 443 at coupling point 444. An end of resistor 442 and resistor 443 can electrically couple to an inverting end of operational amplifier 460 via coupling point 445. A non-inverting end of operational amplifier 460 can be electrically coupled to earth ground 461.

One end of resistor 431 can be electrically coupled to resistor 442 and resistor 443 via coupling point 445. Resistor 431 can be electrically coupled in series with capacitor 436, resistor 432, capacitor 437, and capacitor 438. Resistor 433 can be electrically coupled in parallel between the series connection of capacitor 436 and resistor 432. Resistor 434 can be electrically coupled between series capacitors 437, 438. Resistor 435 can be electrically coupled in parallel between the series connection point of capacitors 437, 438 and earth ground 439. An output of operational amplifier 460 can be electrically coupled to resistor 480 via coupling point 481. Coupling point 481 can be electrically coupled to the shared electrical connection of resistor 434 and capacitor 438.

FIG. 5A is an example magnitude plot 500 of the frequency response of an inactive (i.e., open compensation switch 470) compensation circuit 420. FIG. 5B is an example phase plot 510 of an inactive (i.e., open compensation switch 470) compensation circuit 420. Both magnitude plot 500 and phase plot 510 show the phase shift when compensation circuit 420 is not active is 0 degrees.

Figure 6A:
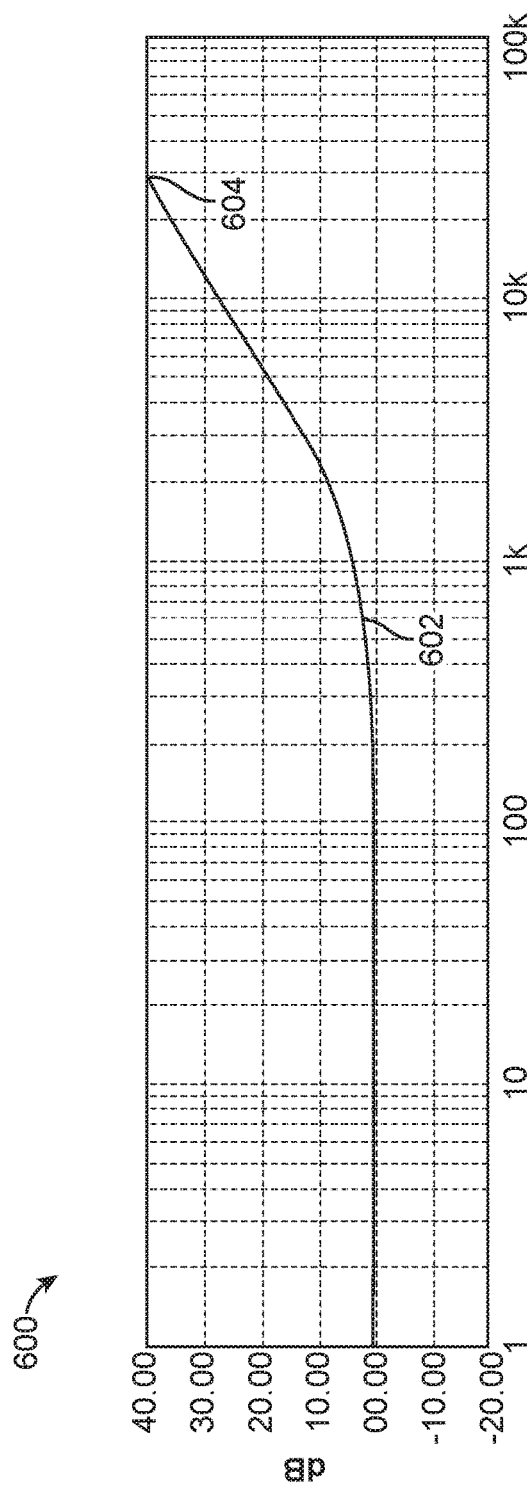
FIG. 6A is an example magnitude plot of the frequency response of an active compensation circuit.
Figure 6B:
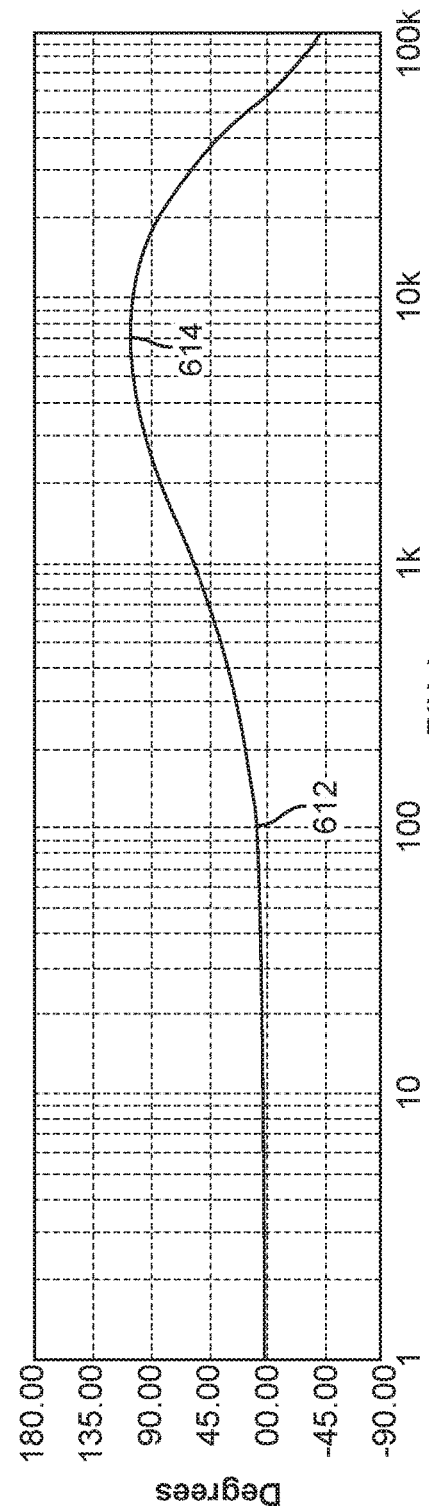
FIG. 6B is an example phase plot of an active compensation circuit.

FIG. 6A is an example magnitude plot 600 of the frequency response of an active (i.e., closed compensation switch 470) compensation circuit 420. Beyond 0 dB, at frequencies higher than about 500 Hz, compensation circuit 420 provides a magnitude boost starting at approximately boost point 602 and increasing up to a maximum boost point 604 of approximately 40 dB at 30 kHz. FIG. 6B is an example phase plot 610 of an active (i.e., closed compensation switch 470) compensation circuit 420. An active compensation circuit 420 also adds a phase lead starting at lead point 612 with a peak phase lead of approximately 105 degrees at 7 kHz at peak phase point 614.

Figure 7:
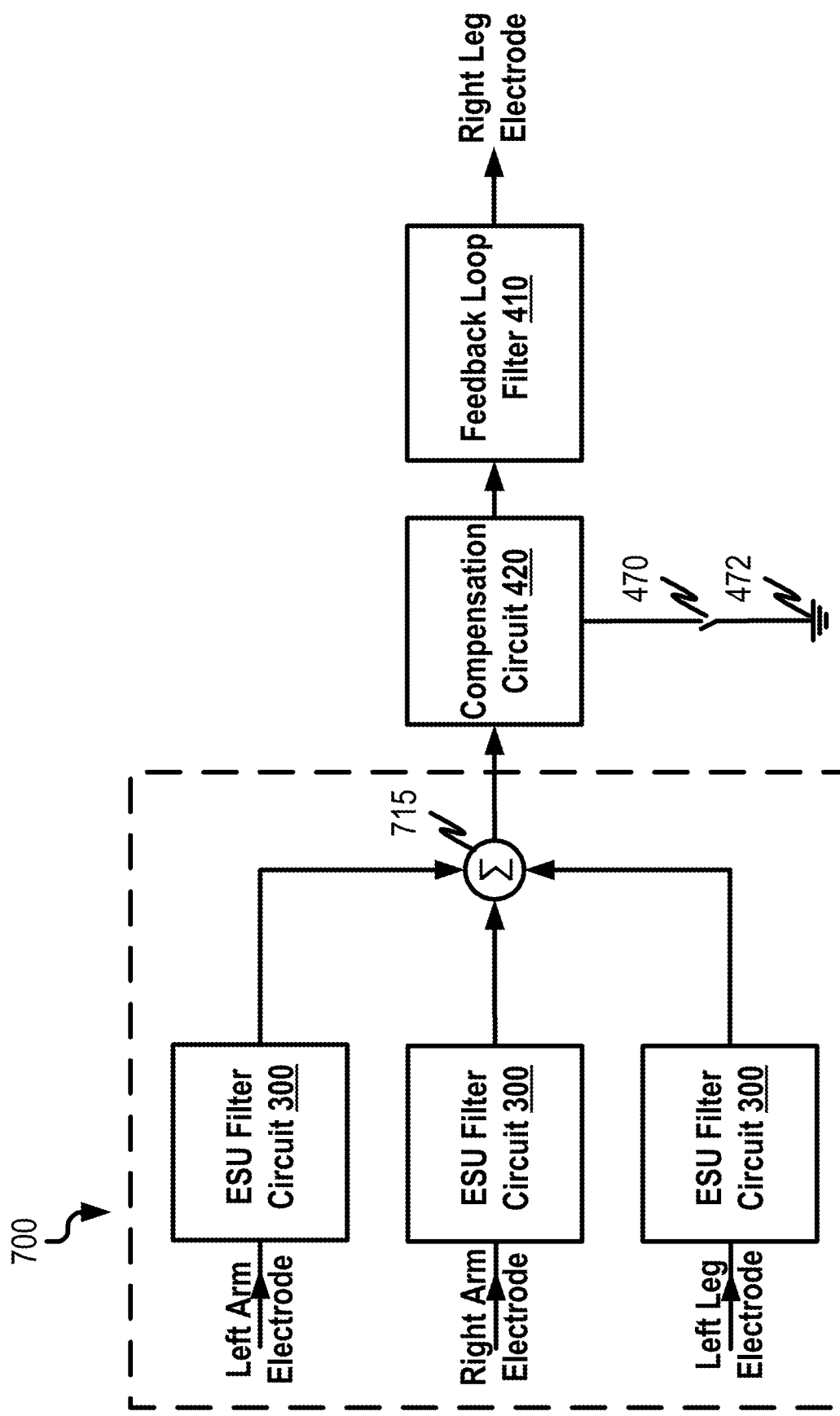
FIG. 7 is a partial system block diagram illustrating an example implementation of the neutral drive feedback loop.

FIG. 7 is a partial system block diagram 700 illustrating an example implementation of the neutral drive feedback loop. Some electrodes of electrode set 120 can be connected to individual ESU filter circuits 300. For example, electrodes of electrode set 120 can include a left arm electrode, right arm electrode, and left leg electrode. Each electrode can be connected to a corresponding ESU filter circuit 300. Output of each ESU filter circuit 300 can be input into a Wilson Average circuit 715. The individual electrodes and Wilson Average circuit 715 can belong to plant 710.

An output of Wilson Average circuit 715 can be connected to compensation circuit 420 that is activated as described herein by compensation switch 470. Output of compensation circuit 420 can be provided to feedback loop filter circuit 410. Output of feedback loop filter circuit 410 can be provided to an electrode of electrode set 120 such as a right leg electrode.

Figure 8:
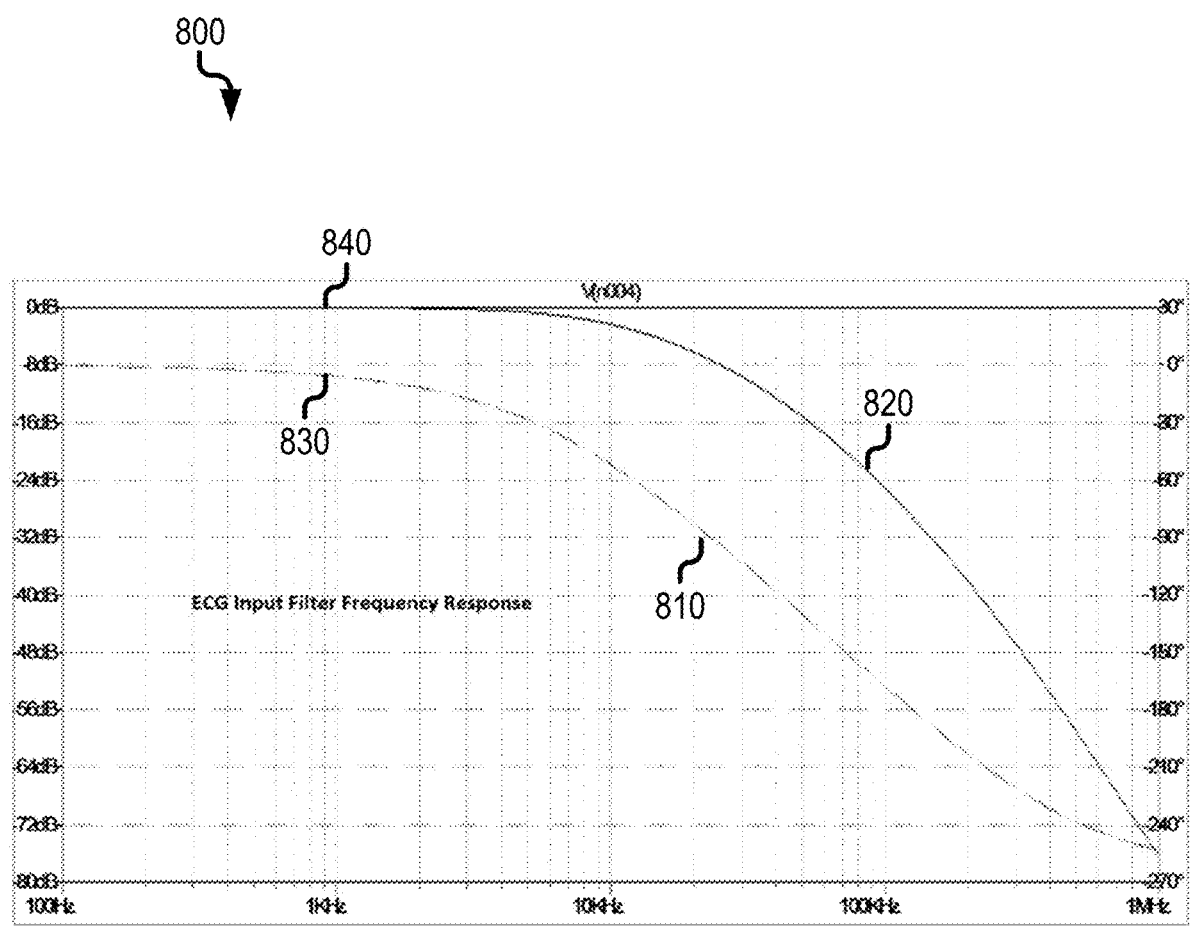
FIG. 8 is an example plot of a normal mode frequency response for an electrode set.

FIG. 8 is an example plot 800 of a normal mode frequency response (i.e., no detected ESU signal) of electrodes of electrode set 120 (i.e., plant 710 frequency response). With no detected ESU signal, ESU filter circuit 300 is not switched in. Plot 800 displays a normal mode plant response of plant 710 used during design of neutral drive feedback loop circuit 400. Plot 800 has a −3 dB cut-off frequency of approximately 10 kHz. Plot 800 includes phase component 810 and magnitude component 820.

Figure 9:
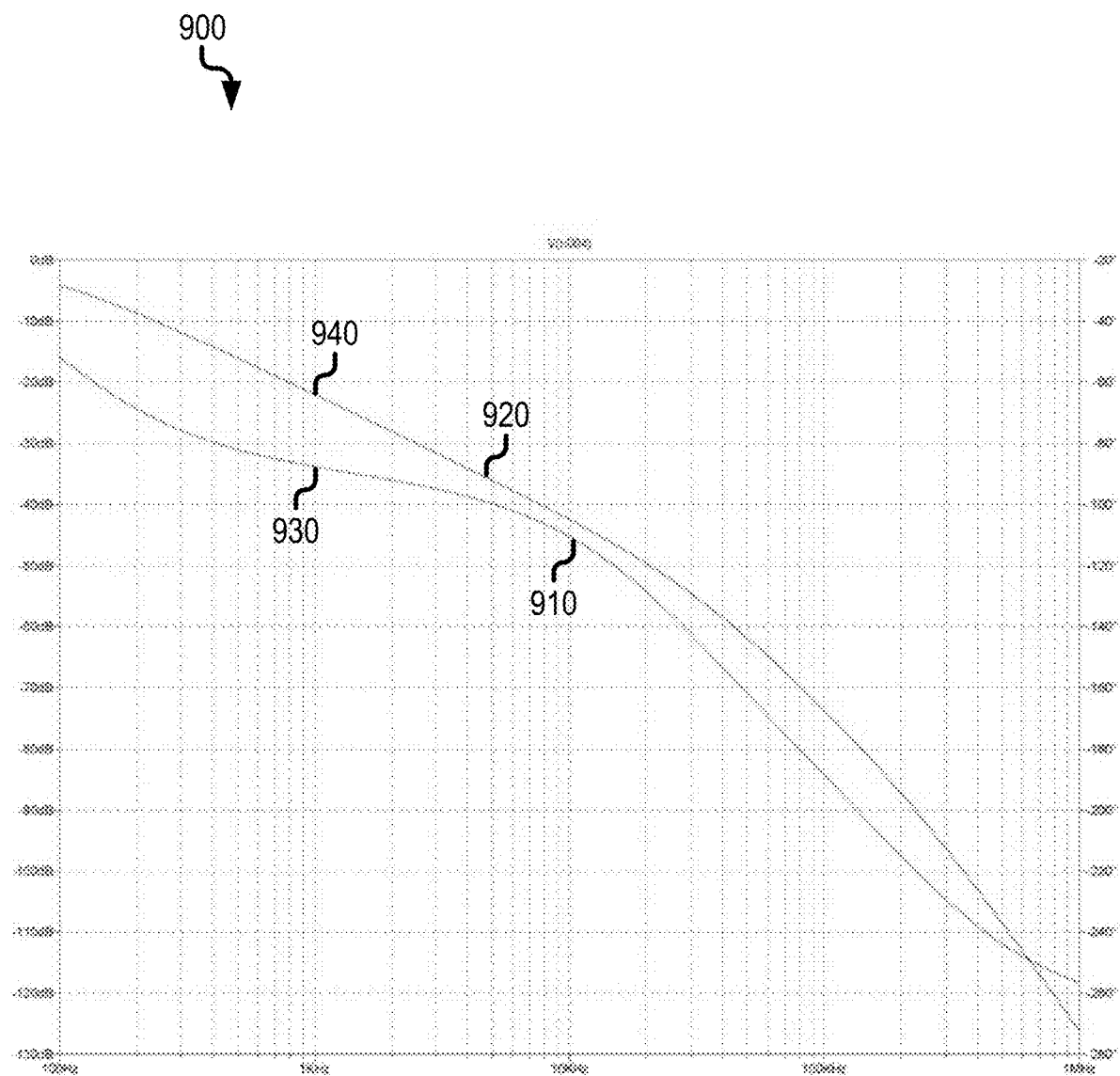
FIG. 9 is an example plot of a frequency response of an electrode set with an active ESU filter circuit.

FIG. 9 is an example plot 900 of a frequency response of an electrode set 120 with an active ESU filter circuit 300 (i.e., plant 710 frequency response). In this case, ESU filter switch 370 is active, filtering out the ESU signal. Plot 900 includes phase component 910 and magnitude component 920. The −3 dB cut-off frequency of dominant pole of ESU filter circuit 300 is approximately 80 Hz.

Effects of the low frequency dominate pole of ESU filter circuit 300 can be found by comparing plot 800 to plot 900 at a frequency of approximately 1 kHz. For example, phase component 910 at phase point 930 lags by approximately 85 degrees compared to phase component 810 at phase point 830, which lags by approximately 7.5 degrees. The ESU filter magnitude component 920 is approximately −22.5 dB at magnitude point 940 compared to normal mode magnitude component 820 of approximately 0 dB at magnitude point 840. The frequency response of the feedback loop filter circuit 410 compensates for the extra phase lag imposed by the ESU filter circuit 300 imposed on the Wilson Average signal. The additional poles of the feedback loop filter circuit 410 compensate for additional poles of the ESU filter circuit 300.

Figure 10:
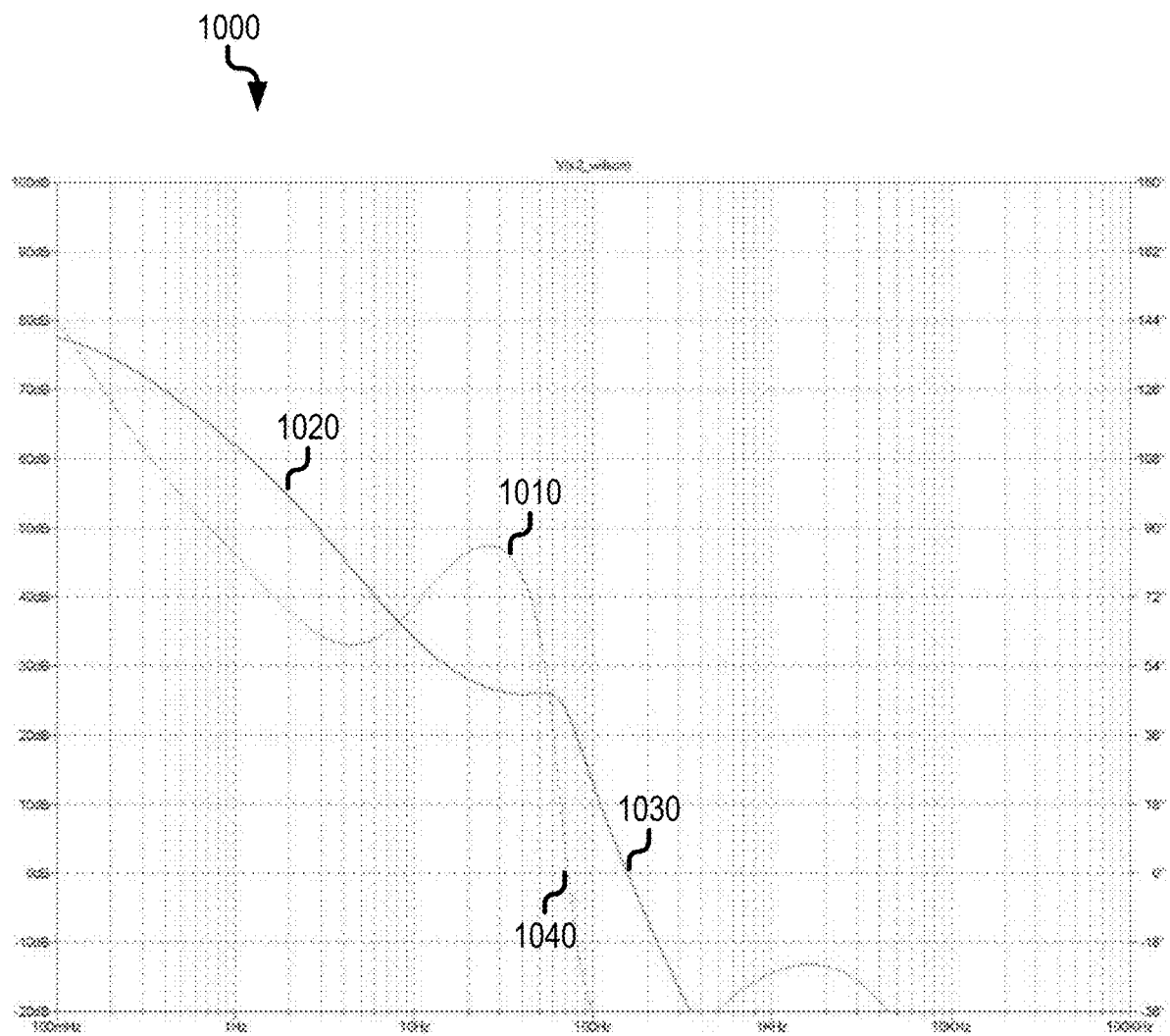
FIG. 10 is an example plot of a frequency response of a neutral drive feedback loop circuit without compensation and with an active ESU filter circuit.

FIG. 10 is an example plot 1000 of a frequency response of a neutral drive feedback loop circuit 400 without compensation and with an active ESU filter circuit. In this case, compensation switch 470 is not active and compensation circuit 420 does not provide for dominant pole compensation of a dominant pole of ESU filter circuit 300. Plot 1000 includes phase component 1010 and loop gain magnitude component 1020. From plot 1000, loop gain magnitude component 1020 is unstable as indicated by intersection point 1030. Intersection point 1030 displays behavior of phase component 1010 where loop gain magnitude component 1020 crosses 0 dB at approximately 150 Hz. Phase component 1010 lags loop gain magnitude component 1020 by approximately 180 degrees. As phase component 1010 passes through phase lag point 1040 at approximately 70 Hz, there is approximately a 180 degree lag. Phase component 1010 does not rise above the 180 degree lag before loop gain magnitude component 1020 crosses 0 dB at intersection point 1030.

Figure 11:
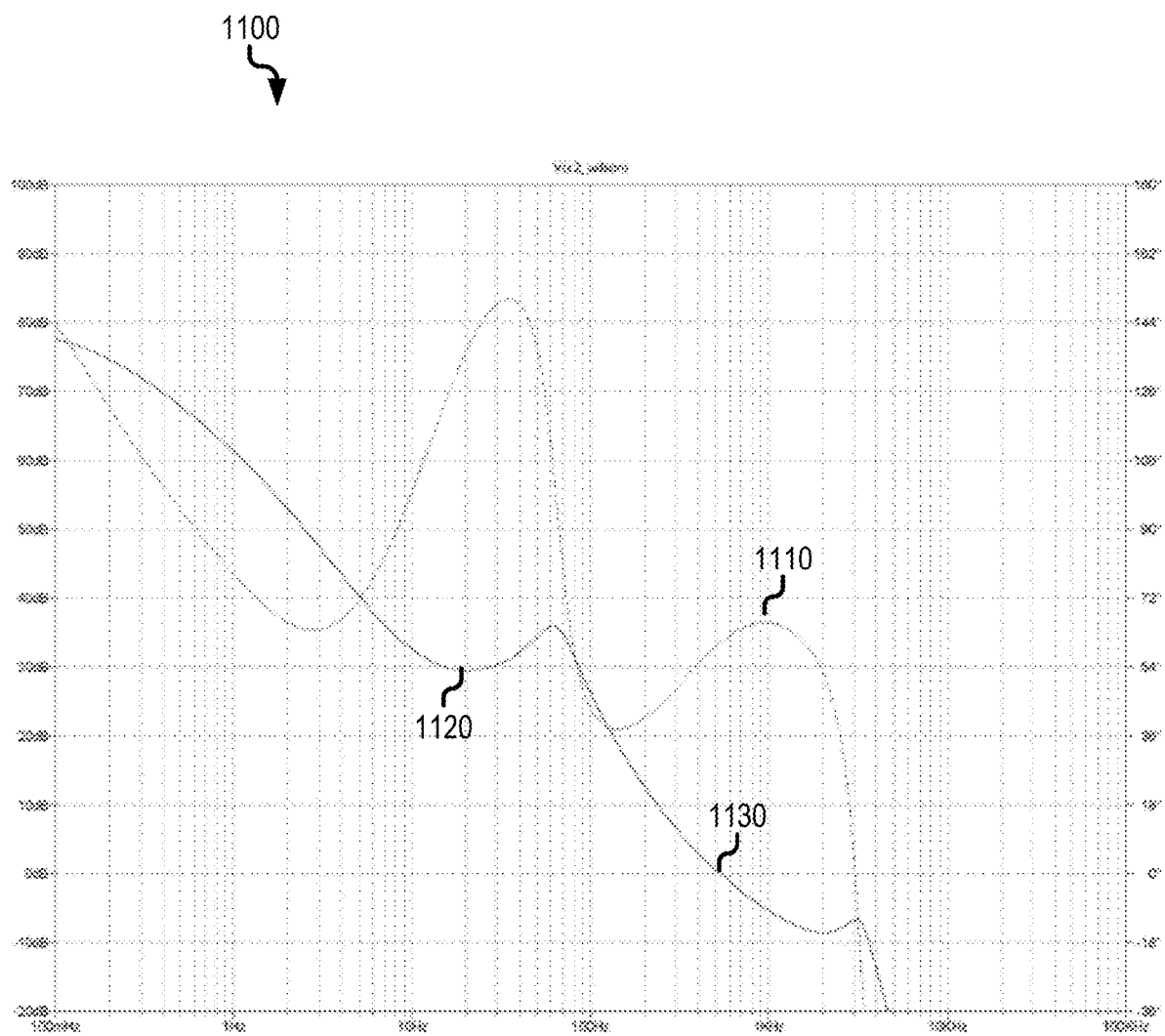
FIG. 11 is an example plot of a frequency response of a neutral drive feedback loop circuit with an active ESU filter circuit and active compensation circuit with compensation for a dominant pole of the ESU filter circuit.

FIG. 11 is an example plot 1100 of a frequency response of neutral drive feedback loop circuit 400 with an active ESU filter circuit 300 and an active compensation circuit 420 compensating for a dominant pole of ESU filter circuit 300. Plot 1100 includes phase component 1110 and loop gain magnitude component 1120. Loop gain magnitude component 1120 intersects 0 dB at intersection point 1130 at approximately 550 Hz. Phase component 1110 shows that there is a phase margin of approximately 60 degrees.

Figure 12:
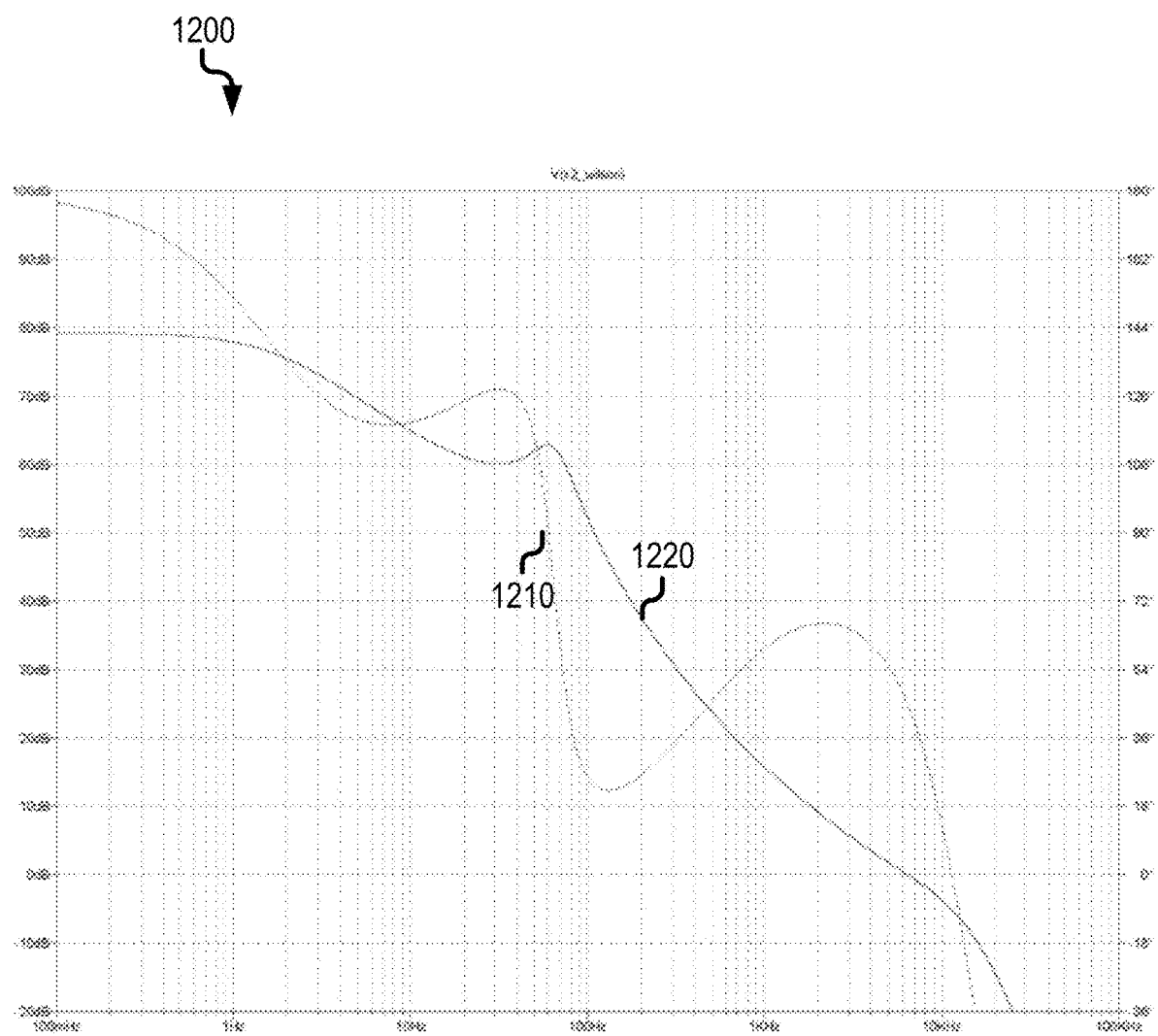
FIG. 12 is an example plot of a frequency response of a normal mode neutral drive feedback loop circuit with an inactive ESU filter circuit, an inactive compensation circuit, and no detected ESU signal.

FIG. 12 is an example plot 1200 of a frequency response of a normal mode neutral drive feedback loop circuit with an inactive ESU filter circuit 300 and an inactive compensation circuit 420 and no detected ESU signal. Plot 1200 includes phase component 1210 and loop gain magnitude component 1220.

Figure 13:
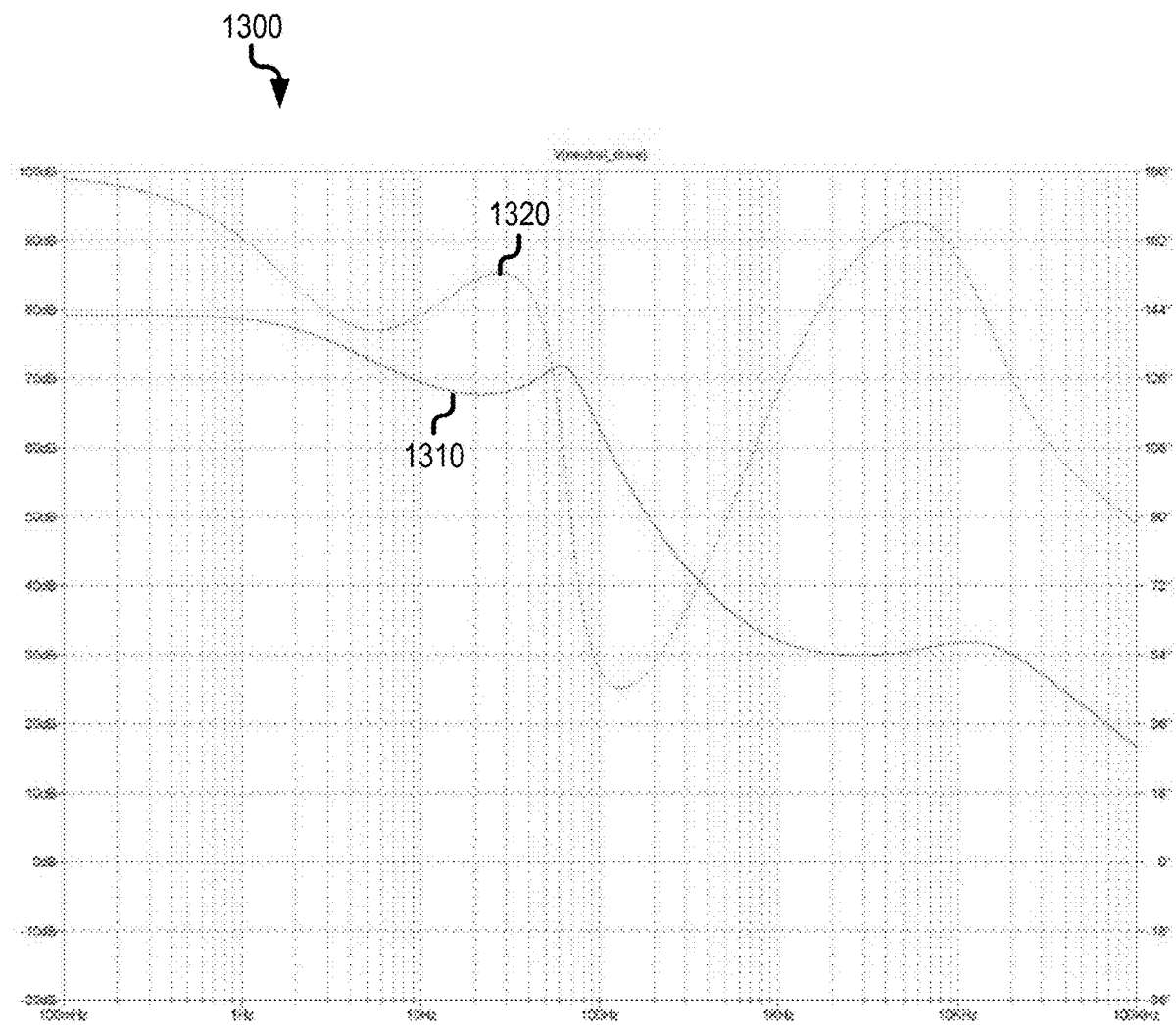
FIG. 13 is an example plot of a frequency response of a neutral drive feedback loop filter circuit for normal mode with an inactive ESU filter circuit, an inactive compensation circuit, and no detected ESU signal.

FIG. 13 is an example plot 1300 of a frequency response of neutral drive feedback loop filter circuit 410 for normal mode (i.e., no detected ESU signal) with an inactive ESU filter circuit 300, an inactive compensation circuit 420, and no detected ESU signal. Plot 1300 includes phase component 1310 and magnitude component 1320.

Figure 14:
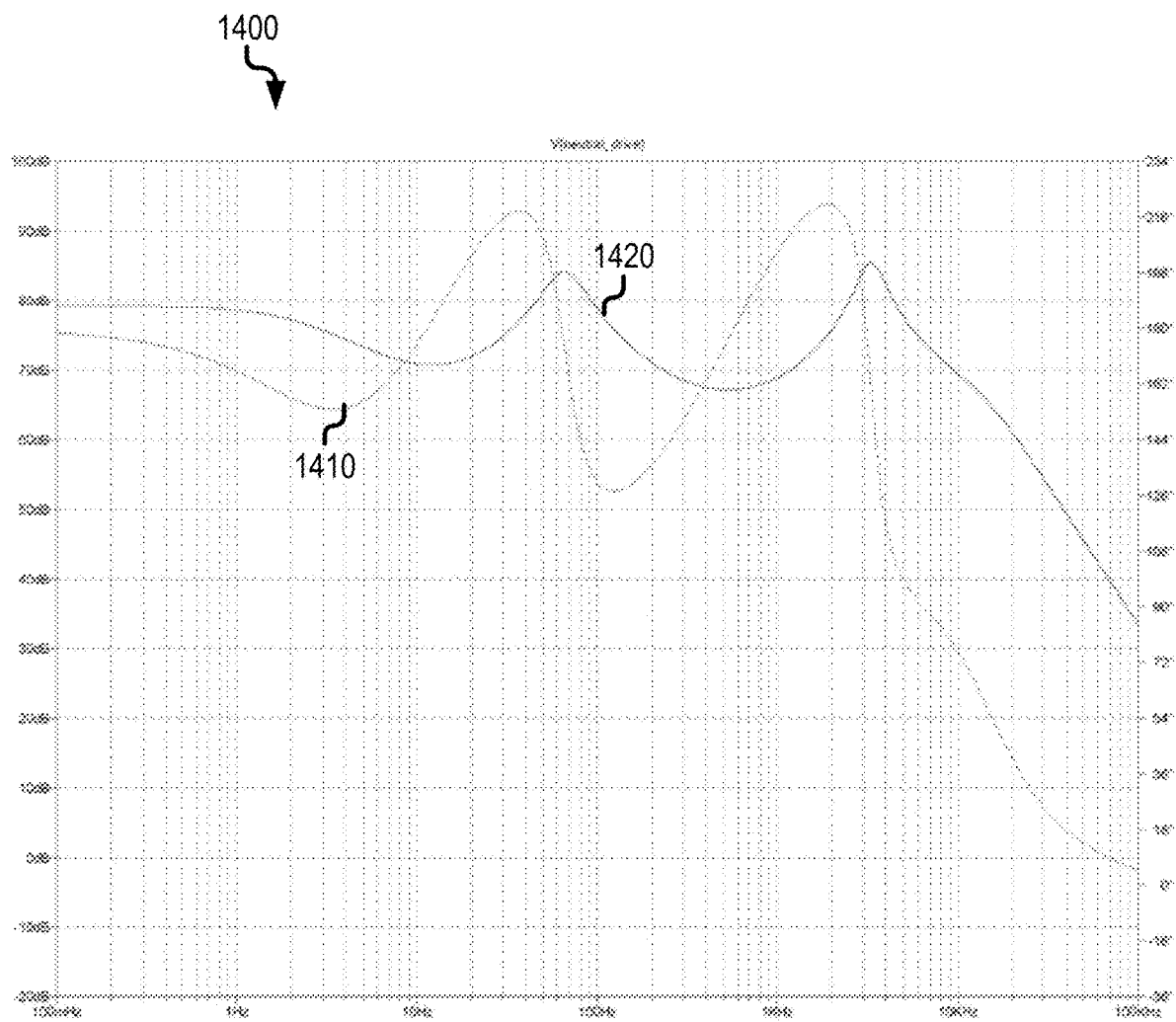
FIG. 14 is an example plot of a frequency response of a neutral drive feedback loop filter circuit with an ESU detected signal, an active ESU filter circuit, an active compensation circuit providing compensation for a dominant pole of the ESU filter circuit.

FIG. 14 is an example plot of a frequency response of neutral drive feedback loop filter circuit 410 with an ESU detected signal, an active ESU filter circuit 300, and an active compensation circuit 420 providing compensation for a dominant pole of the ESU filter circuit 300. Plot 1400 includes phase component 1410 and magnitude component 1420.

Figure 15:
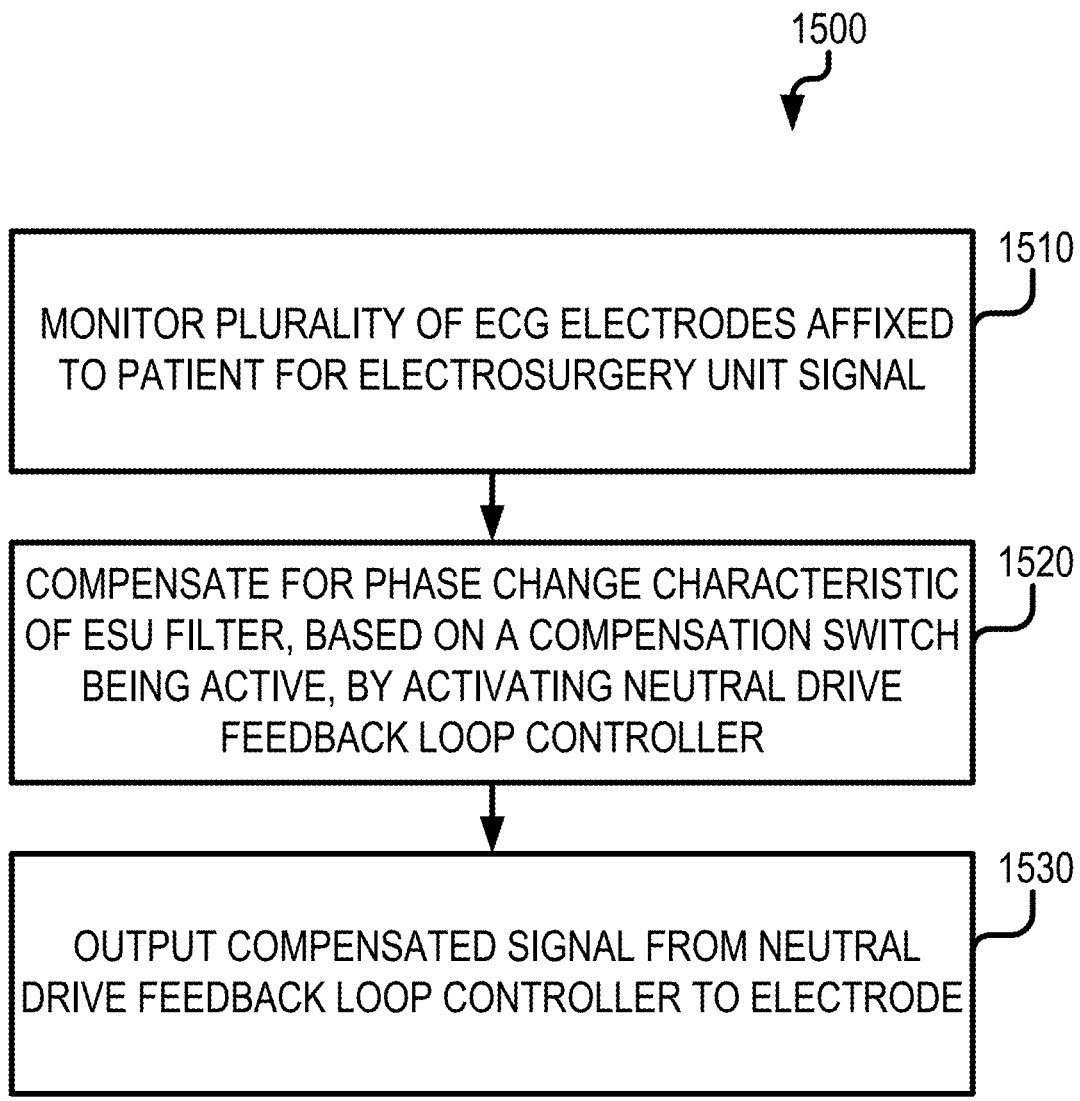
FIG. 15 is an example process flow diagram of neutral drive feedback loop compensation.

FIG. 15 is an example process flow diagram 1500 of neutral drive feedback loop compensation. A plurality of ECG electrodes of electrode set 120 affixed to the patient 110 can be monitored, at 1510, for an ESU signal. Based on compensation switch 470 being active, a phase change characteristic of the ESU filter circuit 300 can be compensated for, at 1520 based on the active compensation switch 470, by a neutral drive feedback loop circuit. This monitoring can occur by detecting an ESU signal using an ESU signal detection circuit 200 and activating an ESU filter circuit 300 and compensation circuit 420 via compensation switch 470. A compensated signal from the neutral drive feedback loop circuit 400 can be output, at 1530, to an electrode of electrode set 120. The electrode can be a right leg electrode.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system can include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

In the descriptions above and in the claims, phrases such as "at least one of" or "one or more of" can occur followed by a conjunctive list of elements or features. The term "and/or" can also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations can be within the scope of the following claims.

What is claimed is:

1. An apparatus comprising: an electrosurgery unit (ESU) signal detection circuit configured to (i) receive an input signal from a first electrode from among a plurality of electrocardiogram (ECG) electrodes, when the first electrode is electrically coupled to a patient, and (ii) output an output signal that indicates detection of an ESU voltage in the input signal; an ESU filter circuit comprising an ESU filter switch electrically coupled to an output of the ESU signal detection circuit, the ESU filter switch being in an active state when the ESU signal detection circuit outputs the output signal that indicates detection of the ESU voltage in the input signal; and a neutral drive feedback loop circuit comprising a compensation switch electrically coupled to the output of the ESU signal detection circuit, wherein when the compensation switch is in an active state, the neutral drive feedback loop circuit is configured to compensate for a phase change characteristic of the ESU filter circuit by outputting a compensated signal to a second electrode from among the plurality of electrodes, when the second electrode is electrically coupled to the patient, and wherein the phase change characteristic of the ESU filter circuit occurs when the ESU filter switch is in the active state, and the compensated signal output by the neutral drive feedback loop circuit compensates for an effect of the phase change characteristic of the ESU filter circuit.

2. The apparatus according to claim 1, wherein the ESU signal detection circuit comprises:
  a peak voltage detector configured to measure an ESU voltage level;
  a threshold circuit configured to set a threshold voltage for comparison with the measured ESU voltage level; and
  an ESU signal operational amplifier configured to compare the threshold voltage and the measured ESU voltage level.

3. The apparatus according to claim 2, wherein the peak voltage detector comprises:
  a series resistor-capacitor (RC) circuit, wherein an electrode input signal is connected to a resistor of the series RC circuit;
  a parallel inductor diode circuit having a first diode and an inductor, the parallel inductor diode circuit electrically coupled between a capacitor of the series RC circuit and earth ground;
  a second diode electrically coupled in series with the parallel inductor diode circuit, wherein an anode end of the second diode is connected to a cathode end of the first diode; and a parallel RC circuit electrically coupled between a cathode end of the second diode and earth ground,
  wherein the measured ESU voltage level is measured across the parallel RC circuit.

4. The apparatus according to claim 2, wherein an inverting input of the ESU signal operational amplifier is connected to the threshold voltage and a non-inverting input of the ESU signal operational amplifier is connected to the measured ESU voltage level.

5. The apparatus according to claim 2, wherein at least one of the compensation switch and the ESU filter switch is active based on an output of the ESU signal operational amplifier being high.

6. The apparatus according to claim 2, wherein the peak voltage detector is frequency selective with a maximum sensitivity range of about 100 kHz to 1 MHz.

7. The apparatus according to claim 1, wherein the neutral drive feedback loop circuit comprises:
  a first resistor and a second resistor;
  a first operational amplifier and a second operational amplifier, each operational amplifier having an inverting input, a non-inverting input, and an output;
  a parallel resistor-capacitor (RC) circuit electrically coupled between an input of the neutral drive feedback loop circuit and the first resistor, wherein the first resistor is electrically coupled between the parallel RC circuit and earth ground at a first coupling point, the first coupling point connected to the non-inverting input of the first operational amplifier;
  a compensation circuit;
  a series RC circuit electrically coupled in parallel to the second resistor, wherein the second resistor is electrically coupled in series with the output of the first operational amplifier and the inverting input of the second operational amplifier;
  a first circuit electrically coupled in parallel between the non-inverting input of the second operational amplifier and the output of the second operational amplifier, the first circuit including at least five resistors and at least three capacitors; and
  an output resistor having a first output terminal and a second output terminal,
  wherein the first output terminal is electrically coupled to the output of the second operational amplifier, and an output of the neutral drive feedback loop circuit includes the second output terminal.

8. The apparatus according to claim 7, wherein the compensation circuit comprises:
  a first resistor having a first terminal and a second terminal and a second resistor having a first terminal and a second terminal, wherein the second terminal of the first resistor is electrically coupled to the first terminal of the second resistor at a first coupling point;
  a first series resistor-capacitor (RC) circuit electrically coupled in parallel on a resistor end to the first coupling point; and
  a second RC circuit electrically coupled to in parallel on a resistor end to the first terminal of the first resistor,
  wherein capacitor ends of the first series RC circuit and the second series RC circuit are electrically coupled to the compensation switch, the compensation switch electrically coupled to earth ground.

9. The apparatus according to claim 8, wherein the first terminal of the first resistor of the compensation circuit and the second terminal of the second resistor of the compensation circuit are each coupled to the neutral drive feedback loop circuit.

10. The apparatus according to claim 1, wherein the ESU filter circuit comprises:
  at least two resistors electrically coupled to one another in series;
  a first diode and a second diode electrically coupled to one another in series at a coupling point, wherein the coupling point coupled an anode end of the first diode to a cathode end of the second diode and the at least two resistors are electrically coupled to the first diode and the second diode at the coupling point;
  a capacitor having one end electrically coupled to the coupling point; and
  the ESU filter switch electrically coupled between another end of the capacitor and a signal ground.

11. The apparatus according to claim 10, wherein the at least two resistors are defibrillator protection resistors.

12. The apparatus according to claim 1, wherein the compensation switch is in the active state when the ESU signal detection circuit outputs the output signal that indicates detection of the ESU voltage in the input signal.

13. The apparatus according to claim 1, wherein input into the neutral drive feedback loop circuit is an average voltage level of the plurality of ECG electrodes, when the plurality of ECG electrodes are affixed to the patient.

14. The apparatus according to claim 1, wherein input to the ESU signal detection circuit is a voltage level from the first electrode from among the plurality of ECG electrodes, when the plurality of ECG electrodes are affixed to the patient.

15. The apparatus according to claim 1, wherein input to the ESU filter circuit is a voltage level from an electrode from among the plurality of ECG electrodes, when the plurality of ECG electrodes are affixed to the patient.

16. The apparatus according to claim 1, wherein output of the ESU filter circuit is a voltage level provided to a patient monitor.

17. The apparatus according to claim 1, wherein the compensated signal output by the neutral drive feedback loop circuit is a current that is provided to the second electrode, when the second electrode is affixed to the patient.

18. The apparatus according to claim 1, further comprising a patient monitor.

19. The apparatus according to claim 1, wherein a frequency response of the neutral drive feedback loop circuit compensates for the phase change characteristic when the compensation switch is in the active state.

20. The apparatus according to claim 1, wherein the phase change characteristic is a dominant pole.

21. The apparatus according to claim 1, wherein when the plurality of ECG electrodes are affixed to the patient, the plurality of ECG electrodes include, a right arm electrode, a left arm electrode, and a left leg electrode.

22. A method comprising:
receiving, using an electrosurgery unit (ESU) signal detection circuit an input signal from a first electrode from among a plurality of electrocardiogram (ECG) electrodes, the first electrode being electrically coupled to a patient;
when detecting an ESU voltage in the input signal, switching an ESU filter switch into an active state, the ESU filter switch being included in an ESU filter circuit; and
when a compensation switch included in a neutral drive feedback loop circuit is in an active state, compensating for a phase change characteristic of the ESU filter circuit by outputting a compensated signal to a second electrode from among the plurality of electrodes, the second electrode being electrically coupled to the patient,
wherein the phase change characteristic of the ESU filter circuit occurs when the ESU filter switch is in the active state, and the compensated signal compensates for an effect of the phase change characteristic of the ESU filter circuit.

* * * * *